(12) United States Patent
Norris

(10) Patent No.: US 6,707,257 B2
(45) Date of Patent: Mar. 16, 2004

(54) FERRITE STABILIZED LED DRIVE

(75) Inventor: Mark A. Norris, Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/215,908

(22) Filed: Aug. 8, 2002

(65) Prior Publication Data

US 2004/0030230 A1 Feb. 12, 2004

(51) Int. Cl.[7] ............................................. H05B 37/02
(52) U.S. Cl. ....................... 315/149; 315/291; 315/307; 345/82; 600/323; 600/310
(58) Field of Search ................. 315/149, 291, 315/307, 169.3; 345/82, 80, 77, 84; 600/323, 310

(56) References Cited

U.S. PATENT DOCUMENTS

| | | | | |
|---|---|---|---|---|
| 5,307,337 A | * | 4/1994 | Woloszczuk | ................ 369/121 |
| 6,097,159 A | * | 8/2000 | Mogi et al. | ................ 315/151 |
| 6,242,870 B1 | * | 6/2001 | Koyanagi et al. | ........... 315/291 |
| 6,253,097 B1 | * | 6/2001 | Aronow et al. | ............. 600/310 |
| 6,490,466 B1 | * | 12/2002 | Fein et al. | .................... 600/323 |
| 6,510,168 B1 | * | 1/2003 | Kikuchi | ....................... 315/149 |
| 6,597,933 B2 | * | 7/2003 | Kiani et al. | ................. 600/323 |

* cited by examiner

Primary Examiner—James Clinger
Assistant Examiner—Ephrem Alemu
(74) Attorney, Agent, or Firm—Marsh Fischmann & Breyfogle LLP

(57) ABSTRACT

An oximeter diode-driving device has a diode, a transistor operative to controllably connect current to the diode, a current sensing resistor that senses at least part of the current, a feedback amplifier operative to control the connecting of current by the transistor according to the current sensed by the current sensing resistor, and an inductor disposed in series with the current sensing resistor. A method of driving a current through the diode of an oximeter includes driving a current through the diode by connecting the current to the diode, controlling the connecting using a feedback type amplifier, the feedback type amplifier having a current source that uses a current-limiting resistor, and adding phase lead to a current passing through the current-limiting resistor.

11 Claims, 2 Drawing Sheets

FERRITE STABILIZED LED DRIVE

CROSS REFERENCE TO RELATED APPLICATIONS

This application incorporates by reference U.S. patent application Ser. No. 10/251,878 titled "Feedback-Controlled LED Switching", and U.S. patent application Ser. No. 10/215,935 titled "Nulled Op-Amp Current Feedback", both filed Aug. 8, 2002.

BACKGROUND OF THE INVENTION

1. Field of the Invention

This invention relates generally to feedback control of oximeter diode drive currents and, more particularly, to eliminating oscillations due to diode cable reactances without degrading current control.

2. Related Work

A pulse oximeter is a type of blood gas monitor which non-invasively measures an amount of saturation of oxygen in the blood. The saturation of oxygenated blood may be determined from the differential absorptions for two plethysmographic waveforms measured at separate wavelengths. The two waveforms are typically produced by driving a visible red light-emitting diode (LED) and an infra-red LED to produce two lights that pass through a patient's tissue, and then detecting the light on the same or an opposite side of the tissue using one or more photodetectors. The light-emitting LEDs are placed in a probe that is attached to the patient's body in a preferred location for the particular application. Although most conventional oximeters use the red and infra-red LEDs, other devices such as surface emitting laser devices having different wavelengths may also be used, and the number of LEDs can vary according to the specific measurement application. For example, it is known to set a number of laser diodes to be equal to or than the number of blood analytes that are to be measured by the instrument. In the specific field of photoplethysmography, the light beams that are generated by the LEDs must be of sufficient intensity to illuminate the perfused tissue and also be of constant wavelength, since the light absorption of the monitored analyte varies as a function of wavelength.

The probe may be a sleeve or clamp that fits around a patient's finger or earlobe. The LEDs are disposed in the probe, for example, to be positioned on one side of the patient's finger. The probe is electrically connected to an LED drive circuit and to detection measurement and analysis apparatus via a cable of a given length.

The probe also has one or more photodetectors that detect the light, for example, received on an opposite side of the patient's appendage from the LEDs. The received light of different wavelengths is converted into electrical signals by the photodetector. The signals are then electronically processed and analyzed to isolate signals representing a measurement of oxygen saturation of arterial blood.

Ideally, the current source for an oximeter LED simply drives current through the probe cable and into the LED without the current being affected by its transmission through the LED driver circuit and probe cable. However, the characteristics of the cable and LED affect the stability of the oximeter LED drive circuit. Large changes in voltage can occur across the probe cable when the LED turns on or off, where this LED switching can cause the oximeter LED drive circuit to experience oscillation as the LED current control circuit tries to keep up with the changing cable voltage. Therefore, when the diode is switched on and off, an oscillation current (ringing noise) may be superimposed on current flowing through the diode. This oscillation degrades current control, and affects accuracy and sensitivity of oximetry measurements. It is understood that the term "current source" used herein refers to either or both of a sourcing or a current sinking configuration.

This oscillation problem exists because the op-amp used to provide the gain in the feedback circuit is slow, the transistor used to control the current is slow, and the current feedback signal is slower still because of parasitic capacitances. Oscillations result when the combined sluggish response of the op-amp, transistor, and feedback is so slow that the feedback response contributes to amplifying the next oscillation instead of contributing to damping. This sluggishness of response is commonly called "phase lag," the condition of oscillating occurring when the phase lag is greater than 180 degrees and when the circuit is still amplifying (gain greater than 1). When the lag is greater than 180 degrees, the feedback starts to return back to a same part of a cycle, causing oscillation. When the lag is 360 degrees, the feedback comes completely back to the same part of the oscillatory cycle. In this manner, the switching of diode voltages can cause LED cable oscillations.

Conventional methods for addressing oximeter diode driver performance have included, for example, setting respective references for the drive voltage at a first voltage level and a second voltage level, and then supplying current to emitter circuits only when the drive voltage is at a first voltage level. Such a method sets the selected voltage reference to a value that determines the magnitude of the desired drive current. However, such conventional systems do not correct a phase lag of a diode drive circuit, but merely compensate for a slow voltage rise time by adjusting a corresponding timing for supplying a drive current.

As noted above, the switching of voltages in an oximeter can cause LED cable oscillations. This problem is compounded by the need for lowering a power consumption and cost of an oximeter. The conventional diode drive circuit discussed above is inefficient and expensive because it requires multiple reference amplifiers and prolonged stabilization periods between switching. Such a drive circuit necessitates a changing of timings for driving the diode Another conventional oximeter diode drive circuit attempts to compensate for lag by lowering the slew rate of the output voltage to the diode, and by using additional load capacitance. However, the voltage across the capacitor will bleed down, causing a power loss, and oximeter performance is reduced significantly by a decoupling of the drive current to the diode. In addition, adding the load capacitor does not reduce a generation of front end noise, does not stabilize a control of the current driving, and does not eliminate any noise from a drive circuit itself.

An additional conventional method uses a low gain in a feedback loop of a driver circuit. However, this greatly reduces a performance of a driver circuit and also does not actually reduce noise, but merely reduces a dynamic range for diode drive current control and reduces an amplitude of a resultant ringing.

What is needed is a method and apparatus for stabilizing the driving of a current through a diode of an oximeter, where a low cost and a low power consumption are achieved along with tight control of the current through the diode. In addition, a clean diode current source with expanded dynamic range is needed for improving resolution and signal-to-noise ratio in oximetry systems. The effects of front-end, diode current noise are compounded by a use, for example, of laser diodes, which have very non-linear characteristics compared with conventional LEDs. This non-linearity of a laser diode means that a high-bandwidth laser diode cannot withstand an overcurrent state due to oscillations, even for a short period of time. As a result, conventional diode drive circuits may cause a complete breakdown of a laser diode. An example of a use of laser diodes in pulse oximetry is disclosed in U.S. Pat. No. 6,253,097 to Aronow, et al., which is incorporated by reference in its entirety.

SUMMARY OF THE INVENTION

It is an object of the present invention to prevent oscillations caused by sluggish performance of a diode driver circuit.

It is another object of the present invention to correct phase lag of a diode driver circuit without requiring that a timing of switching of the diode be changed.

It is a further object of the present invention to improve over conventional diode driver circuits by allowing for faster switching and more accurate control of multiple diodes.

It is an additional object of the present invention to stabilize a feedback type current source with a low-cost ferrite bead.

It is a still further object of the present invention to stabilize a current source that includes a current-sensing feedback arrangement.

It is yet another object of the present invention to identify a noise source in a diode current sourcing circuit and then reduce that noise, with or without affecting a current passing through the diode.

It is another object of the present invention to maintain a tight control of diode current in a diode driver circuit of an oximeter.

The present invention provides an apparatus including an amplifier having feedback, a resistor that senses a current being input to the amplifier, and an inductor that adds phase lead to the current.

A method for driving a current through a diode of an oximeter according to the present invention includes sensing a current of a signal being input to a feedback type amplifier, adding phase lead to the signal being input to the feedback type amplifier, and driving a diode with at least part of the signal having added phase lead.

A method for driving a current through a diode of an oximeter according to the present invention includes driving a current through the diode by connecting the current to the diode, controlling the connecting using a feedback type amplifier, the feedback type amplifier having a current source that uses a current-limiting resistor, and adding phase lead to a current passing through the current-limiting resistor.

An oximeter diode-driving device according to the present invention includes a diode, a transistor operative to controllably connect current to the diode, a current sensing resistor that senses at least part of the current, a feedback amplifier operative to control the connecting of current by the transistor according to the current sensed by the current sensing resistor, and an inductor in series with the current sensing resistor.

As a result of implementing the present invention, oscillations due to diode cable probe reactances are reduced or eliminated without degrading current control. In addition, dynamic range is increased, and power consumption and cost are reduced.

These and other objects, features, and advantages of the present invention will become more apparent when considered in connection with a detailed description of preferred embodiments, which are illustrated in the accompanying drawing figures.

This summary does not limit the invention, which is instead defined by the appended claims.

BRIEF DESCRIPTION OF THE DRAWING FIGURES

DETAILED DESCRIPTION OF A PREFERRED EMBODIMENT

In general, none of the prior art has considered specific causes of LED drive current noise, including oscillations. This is because the conventional signal processing for a detected oximetry signal was unable to detect, discern, or distinguish any noise as being due to the diode driving circuit. Conventional oximetry systems have not attempted to provide a "clean" LED drive circuit with expanded dynamic range, as in the present invention, because a typical detection signal processing did not have the highly increased resolution provided by, for example, oversampling. With advances in the state-of-the-art providing better processing hardware and software, a resultant higher processing capability and greater resolution allows "seeing" smaller noises that were previously unnoticed. Along with improved resolution, it is of paramount importance to reduce or eliminate the noise sources in the LED drive circuitry of an oximeter, rather than separating-out resultant downstream signals during processing of signals from the oximeter's photodetector. The needs for cleaner diode current source circuits are exposed with state-of-the art processing that allows users to see, for the first time, the effects of various front-end noises, such as those due to diode current driving circuits. Since front ends provide more dynamic range, a conventional problem of over-ranging is eliminated. The resultant large dynamic range eliminates or greatly reduces a conventional need to change drive levels and gain levels, such as by reducing a number of ranges that are required. The reduced number of ranges, reduced number of switching events, and greatly increased stability also results in there being greatly reduced settling time in the diode driver circuit of the present invention. Since there is minimal settling time, data is not lost or thrown away due to instability. For example, a problem of conventional diode driver circuits is that data is often thrown away during a settling period due to changing and oscillating currents.

Even a small amount of noise in the diode current creates problems in subsequent detecting because the detected signal can be greatly influenced by, e.g., motion artifacts, ambient light, tissue irregularities, etc. By reducing the diode current noise, a corresponding power consumption can also be reduced, and detector resolution and accuracy are improved.

Figure 1:
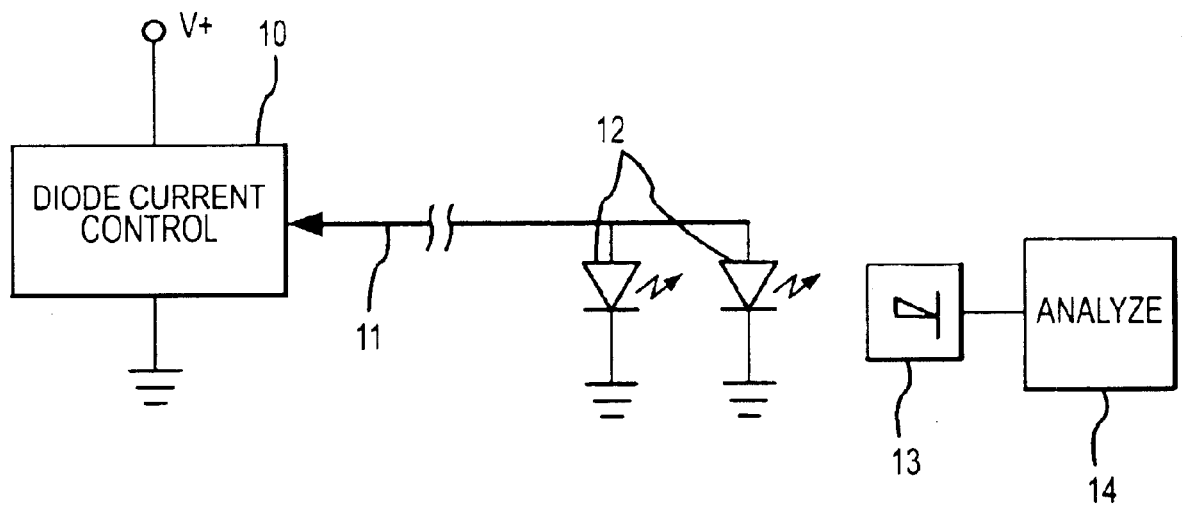
FIG. 1 shows a basic configuration of an oximetry system according to an exemplary embodiment of the present invention.

FIG. 1 is a highly schematic illustration of an oximetry system. A diode current control circuit 10 is connected to one or more LEDs 12 that are used to illuminate a portion of a patient's body in order to measure a blood oxygen level. A light that passes through, or that is reflected from, the patient is detected by photodetector 13. The detected light is converted into electrical signals by the photodetector 13, which passes the electrical signals to a signal analyzer 14. The signal analyzer 14 processes the signals in order to obtain various information that includes the blood oxygen levels. The LEDs 12 are connected to the diode driver circuit 10 with cables 11. The cables 11 may be composed of individual or multiple conductors, and can be shielded or unshielded.

Figure 2:
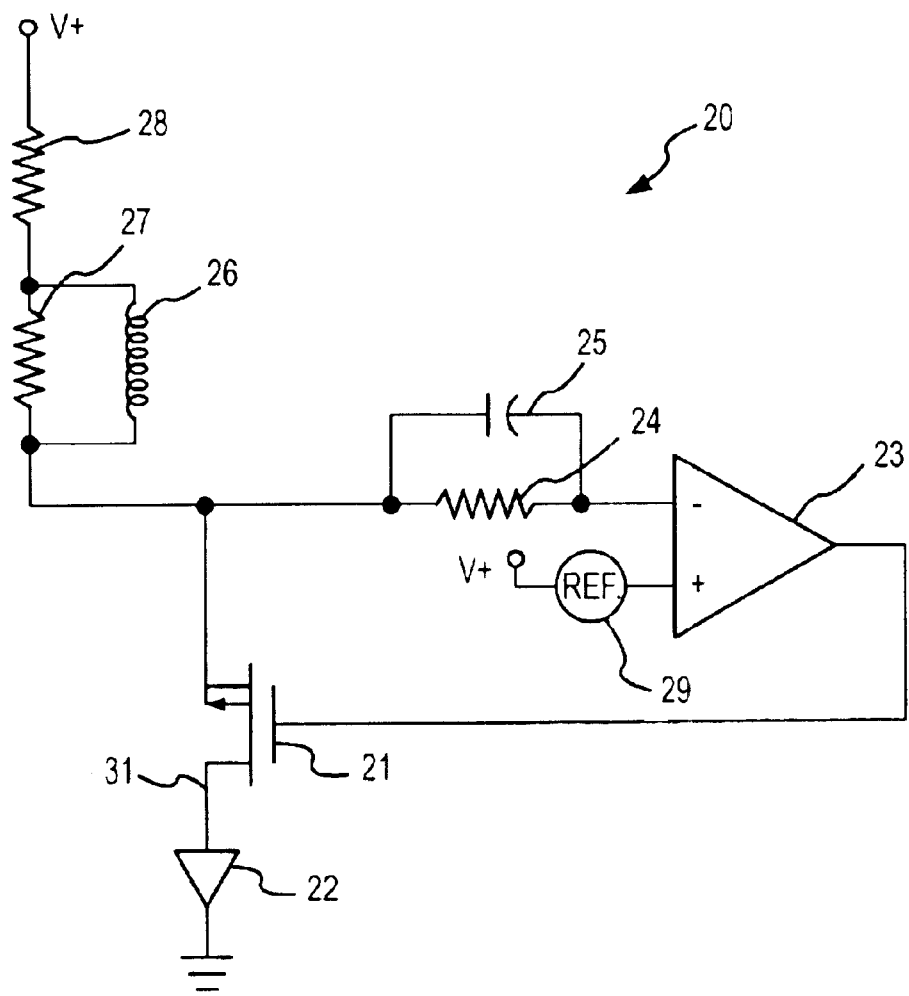
FIG. 2 shows a diode drive circuit according to an exemplary embodiment of the present invention.

FIG. 2 illustrates an exemplary feedback type diode driver circuit according to the present invention. A reference voltage is supplied to the non-inverting input of an op-amp 23 from a reference voltage source 29. The inverting input terminal of the op-amp 23 is connected to one end of a feedback resistor 24 that is in parallel with a feedback capacitor 25. The other end of the parallel combination of feedback resistor 24 and feedback capacitor 25 is connected to the source terminal of PMOS FET 21 and to one end of the parallel combination of inductor 26 and damping resistor 27. The other end of the parallel combination of inductor 26 and damping resistor 27 is connected to one end of a current sensing resistor 28. The other end of the current sensing resistor 28 is connected to positive supply voltage, V+. The output terminal of op-amp 23 is connected to the gate of PMOS FET 21. The drain of PMOS FET 21 is connected to the anode of light emitting diode 22. The cathode of light emitting diode 22 is connected to ground.

The current sensing resistor 28 is the primary input to the feedback circuit 20. The change of the current through current sensing resistor 28 causes a corresponding excitation of, and response from, the inductor 26. The response $\Delta i/\Delta t$ in inductor 26 acts to amplify the effect of changing current in the feedback circuit, thereby advancing a phase of the feedback signal. The FIG. 2 circuit thereby addresses the above-discussed oscillations that can occur when the phase lag is greater than 180 degrees.

Even though inexpensive op-amps are readily available with bandwidths that greatly exceed the low frequency requirements of the oximeter, stability is further increased by selecting an op-amp with a greater bandwidth capability, e.g., a larger gain-bandwidth product. When the switching frequency increases, the relative gain of the op-amp is decreased, and the problem of phase lag can becomes greater. However, in the FIG. 2 circuit, it is most important that noise characteristics of the op-amp 23 be as low as practicable. The LEDs may be turned on at different times, at different rates, or in any manner in which the LEDs can be separated, such as by using a multiplexing scheme. It is important that the rate at which an LED is turned on and off be considered when determining a signal amplitude for each LED.

As shown in FIG. 2, The inductor 26 acts to amplify the effect of changing current being sourced to the amplifier circuit and diode. Therefore, when the current through the feedback loop starts to vary due to ringing in the probe cable 31 caused by switching on and off the diode voltage, the feedback acts more energetically than without the inductor 26 because the increased amplification creates a quicker response. This "energetic" response causes the op-amp 23 to quell the oscillation before the oscillation even has a chance to begin. This is because the inductor 26 adds phase lead to counteract the phase lag caused by sluggishness and parasitic capacitances.

A preferred embodiment uses a ferrite bead as the inductor 26. "Ferrite" is a term conventionally used to describe a wide range of different ceramic ferromagnetic materials. Specifically, ferrite can be used to describe materials with the spinel crystal structures having the general formula $XFe_2O_2$, where X is any divalent metallic ion having the proper ionic radius to fit in the spinel structure. For example, magnesioferrite is a commonly used ferrite. Several ceramic ferromagnetic materials may deviate stoichiometrically from the general formula $XFe_2O_2$, but can also be used for certain ferrite applications.

The conductivity and permittivity of ferrites may be analyzed by modeling ferrites as grains (crystals) of a low-resistance material separated by thin layers of low-conductivity material. The conductivity and permittivity change as a function of frequency of frequency and as a function of the amount of divalent iron ion present in the material. Since ferrites typically have an electrical resistivity that is $10^6$ times that of metals, ferrites have much lower eddy-current losses and are conventionally used at frequencies greater than 10 kHz. Different ferrite compounds are used for different frequency applications. For filtering applications, different properties, such as a temperature coefficient of permeability or a saturation flux density, may dictate a choice of ferrite materials.

A ferrite bead is known as a lossy inductor that can be used to suppress radio frequency (RF) noise, and is conventionally used in a serial configuration to provide electromagnetic interference (EMI) suppression. The ferrite bead is used in the FIG. 2 circuit due to its low cost and small size. A ferrite bead uses ferrite for its core and has an impedance that increases as the frequency becomes higher. At high frequencies, a loss resulting from use of the ferrite core material becomes pronounced, but this is not a problem at the low frequencies used in the diode current control circuit. For example, the diode 12, 22 is typically switched on or off at a frequency of 200 Hz to 10 KHz, although the present invention is not limited to any particular frequency range. However, at the low frequency of oscillations found in LED drives, the Q of such a lossy inductor as the ferrite bead is still too high. Therefore, the damping resistor 27 is required in the FIG. 2 circuit. Even though additional phase lead added by inductor 26 keeps the phase lag of the feedback circuit less than 180 degrees until a time well after a time when the gain of the op-amp 23 has dropped below unity, inductor 26 may itself create oscillations as an LC oscillator, with the same parasitic capacitances it is intended to counteract. In order to minimize such an oscillation, the FIG. 2 circuit uses the damping resistor 27 to dampen these potential oscillations, reducing the Q of the circuit and preventing any self-oscillation effect that can be caused by parasitic capacitance from inductor 26.

The FIG. 2 circuit also has a feedback resistor 24 that is used to isolate the feedback when the diode 22 is off. The op-amp 23 itself has a varying amount of input capacitance seen through feedback resistor 24, which slows the response of the op-amp 23 to the feedback. Therefore, the feedback capacitor 25 is used to lower the capacitance of feedback resistor 24 at high frequencies, in order to counteract the slowing effect of the op-amp 23 input capacitance.

Ideally, a current source for the diode 22 will reduce oscillation and other noise in the diode current without attenuating or significantly reducing control of the diode current. However, an alternative embodiment of the present invention may include an additional transistor capacitor (not shown) that is placed within the diode current control circuit 10 of FIG. 1 to minimize switching noise of a transistor. This transistor capacitor may be used in proximity to the control circuit output to the cable 11. Such a transistor capacitor acts in a manner similar to the inductor 26, whereby the transistor capacitor dampens ringing and oscillations in the diode current due to the sluggishness and lag of the transistor 21 and op-amp 23. Use of the transistor capacitor adds lead to the diode current in a manner similar to the use of inductor 26, but the use of the transistor capacitor also can cause losses that may reduce control of the current at the diode and may increase a power consumption of the diode current driving circuit. For this reason, it is preferred that an inductance value of the inductor 26 be chosen that completely obviates a need for the transistor capacitor.

Figure 3:
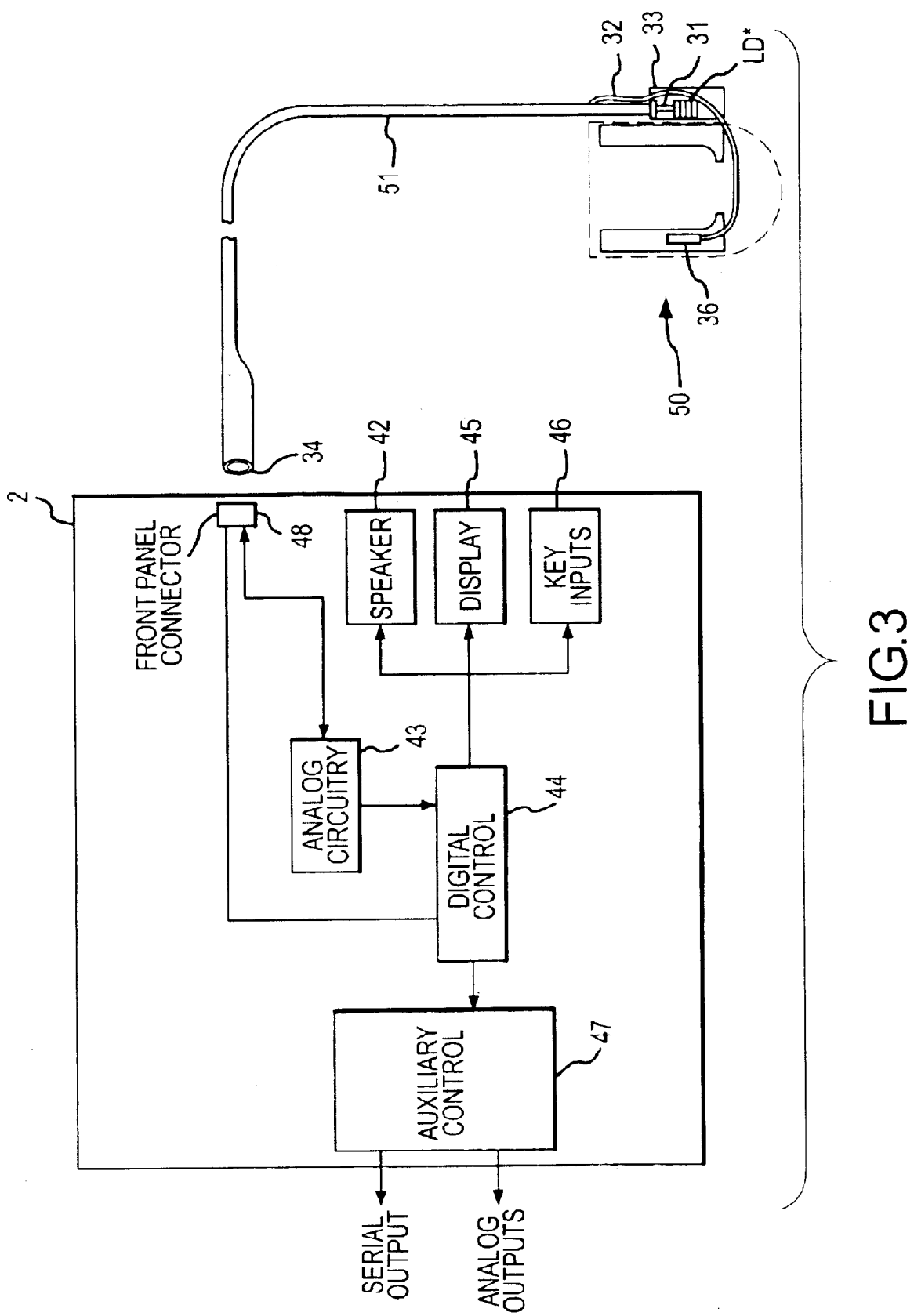
FIG. 3 illustrates a basic architecture of an exemplary pulse oximeter that utilizes a diode drive circuit of the present invention, including a side cutaway view of the probe and a block diagram of the control elements of the monitor.

FIG. 3 shows a basic configuration of an exemplary embodiment of the present invention which utilizes laser diodes. A monitor 2 includes circuitry for obtaining return signals produced by the reception of light passing through the illuminated appendage, and circuitry for user interfacing. The monitor 2 includes analog circuitry 43 which functions to receive and condition the electrical signals produced by the light detector 36 of probe 50. The received signals are digitized and then processed by digital control 44, which outputs computed measurements to display 45 as part of the user interface. A speaker 42 enables the digital control 44 to produce audible alarms to alert the user to error or danger conditions. Key inputs 46 enable the user to input control information to regulate the operation of the instrument. An auxiliary control circuit 47 receives signals from digital control 44 for transmission in serial digital and/or analog form to other elements in the medical monitoring instrument. The cable connector 33 contains the light generation apparatus (laser diodes LD*), optical fiber 32 that connects to the light detector 36 in probe 50, and optical apparatus that applies the light beams generated by the laser diodes LD* to the patient's appendage. The laser diodes can be configured as an array of surface emitting laser diodes. The number of laser diodes LD* is equal to or greater than the number of blood analytes that are to be measured by the instrument. The cable 31 provides the drive current for the laser diodes LD*, the cable 31 being composed of multiple conductors. Cable 31 and optical fiber 32 are both contained within cable 51, which is therefore a hybrid cable contained within a single sheath. The cable 51 is detachably connected to the monitor 2, with the cable connector 34 engaging with the front panel connector 48. In the exemplary FIG. 3 embodiment, the feedback circuit 20, current sensing resistor 28, and inductor 26 are a part of the analog circuitry 43.

Although the exemplary embodiments are described in terms of a voltage-to-current converter configured in a sourcing circuit, the invention can also be implemented using a sinking circuit configuration, by using either laser diodes and optical fiber, or by using conventional visible or infrared diodes with conductive cable.

Although the present invention has been described by reference to exemplary preferred embodiments, the scope of the present invention is not in any way limited to the described embodiments. The present invention is intended to embrace all embodiments that come within the spirit and scope of the following claims, including all equivalent methods and apparatus.

What is claimed is:

1. An oximeter diode-driving device, comprising:
   a diode;
   a transistor operative to controllably connect current to the diode;
   a current sensing element that senses at least part of the current;
   a feedback amplifier operative to control the connecting of current by the transistor according to the current sensed by the current sensing element; and
   an inductor disposed in series with the current sensing element.

2. An oximeter diode-driving device according to claim 1, wherein the diode is a laser diode.

3. An oximeter diode-driving device according to claim 1, wherein the diode is a light-emitting diode.

4. An oximeter diode-driving device according to claim 1, wherein the inductor is a ferrite bead.

5. An oximeter diode-driving device according to claim 1, further comprising a cable connecting the diode to the transistor, wherein an inductance value of the inductor is set to counteract a phase lag caused by at least one of reactance of the cable and capacitance across the transistor.

6. An oximeter diode-driving device according to claim 5, wherein an inductance value of the inductor is set to counteract a phase lag caused by the combined sluggishness of the transistor, feedback amplifier, and cable.

7. An oximeter diode-driving device according to claim 1, further comprising a damping element disposed in parallel with the inductor.

8. An oximeter diode-driving device according to claim 7, wherein a resistance value of the damping element is set based on lowering a Q of the inductor by a predetermined amount.

9. An oximeter diode-driving device according to claim 1, further comprising:
   a feedback capacitor disposed between the transistor and an inverting input of the feedback amplifier; and
   a feedback element disposed in parallel with the feedback capacitor.

10. An oximeter diode-driving device according to claim 9, wherein a capacitance value of the feedback capacitor and a resistance value of the feedback element are set to define an on/off time constant for the feedback amplifier.

11. An oximeter diode-driving device according to claim 10, wherein the capacitance value of the feedback capacitor is set to counteract a phase lag caused by an input capacitance of the feedback amplifier.

* * * * *